(12) United States Patent
Rosa et al.

(10) Patent No.: US 8,658,680 B2
(45) Date of Patent: Feb. 25, 2014

(54) CHEMICALLY STABLE DISPERSIONS OF PROTHIOCONAZOLE AND PROCESSES FOR PREPARING THEM

(75) Inventors: Fred C. Rosa, Wake Forest, NC (US); Tai-Teh Wu, Chapel Hill, NC (US)

(73) Assignee: Bayer Cropscience LP, Research Triangle Park, NC (US)

( * ) Notice: Subject to any disclaimer, the term of this patent is extended or adjusted under 35 U.S.C. 154(b) by 49 days.

(21) Appl. No.: 13/206,077

(22) Filed: Aug. 9, 2011

(65) Prior Publication Data

US 2012/0046328 A1 Feb. 23, 2012

Related U.S. Application Data

(60) Provisional application No. 61/374,386, filed on Aug. 17, 2010.

(51) Int. Cl.
*A61K 31/41* (2006.01)

(52) U.S. Cl.
USPC .......................................................... 514/384

(58) Field of Classification Search
USPC .......................................................... 514/384
See application file for complete search history.

(56) References Cited

U.S. PATENT DOCUMENTS

2008/0254013 A1* 10/2008 Angst et al. ................ 424/93.46

OTHER PUBLICATIONS

Rimer, Jeffrey D. et al., "Crystal Growth Inhibitors for the Prevention of L-Cystine Kidney Stones Through Molecular Desing", Science, vol. 330, No. 337, Oct. 15, 2010, p. 337-341.

* cited by examiner

*Primary Examiner* — Paul Zarek
(74) *Attorney, Agent, or Firm* — Miles & Stockbridge P.C.

(57) ABSTRACT

Chemically stable aqueous dispersions of prothioconazole and processes for preparing them are provided. The dispersions comprise prothioconazole present in an aqueous medium, and a sulfur-containing compound present in an amount effective to render the dispersion chemically stable.

14 Claims, No Drawings

CHEMICALLY STABLE DISPERSIONS OF PROTHIOCONAZOLE AND PROCESSES FOR PREPARING THEM

CROSS-REFERENCE TO RELATED APPLICATIONS

This application claims the benefit of priority of U.S. Provisional Application No. 61/374,386, filed Aug. 17, 2010, and which is hereby specifically incorporated by reference.

FIELD OF THE INVENTION

The present invention is directed to chemically stable aqueous dispersions of prothioconazole and processes for preparing them.

BACKGROUND OF THE INVENTION

In the agricultural chemical industry, triazoles are an important class of fungicides. One such fungicidal triazole is 2-[2-(1-chlorocyclopropyl)-3-(2-chlorophen-yl)-2-hydroxypropyl]-2,4-dihydro-[1,2,4]-triazole-3-thione, also known as prothioconazole. Numerous prothioconazole-based products have been introduced by Bayer CropScience into the market since 2004 under brands such as Proceed®, Proline®, Input® and Prosaro®. The preparation of a number of agricultural microbiocides such as prothioconazole, prepared from triazolyl derivatives, is disclosed in U.S. Pat. No. 5,789,430.

Unfortunately, prothioconazole is subject to chemical degradation, and aqueous dispersions of prothioconazole, in particular, microdispersions, may become chemically unstable, particularly when formulated at low, ready-to-use concentrations, significantly reducing their shelf life. Losses of ten to fifteen percent by weight of the active ingredient over time have been observed in low concentration formulations. In formulations of agricultural chemicals having one or more active ingredients (ai's) that are present at a nominal declaration (label declaration) of greater than 1 percent by weight (1%) but less than 20 percent by weight (20%), current government regulations require that active ingredients be present in amounts that deviate no more than 5 percent by weight from the labeled concentration.]] If the nominal declaration is <1%, the upper and lower certified limits (range) defaults to ±10%; if the nominal declaration is >20% then the upper and lower certified limits (range) defaults to ±3%

It would be desirable to develop chemically stable aqueous dispersions of prothioconazole and processes for preparing them so as not to deviate beyond the certified limit range(s) as established by way of the nominal label declaration.

SUMMARY OF THE INVENTION

Chemically stable aqueous dispersions of prothioconazole and processes for preparing them are provided. The dispersions comprise prothioconazole present in an aqueous medium and a sulfur-containing compound present in an amount effective to render the dispersion chemically stable.

The present invention also provides a process for preparing a chemically stable aqueous dispersion of prothioconazole, the process comprising:

(a) introducing prothioconazole to an aqueous medium to yield an aqueous dispersion of prothioconazole; and (b) introducing a sulfur-containing compound to the aqueous dispersion in an amount effective to render the solution chemically stable.

DETAILED DESCRIPTION OF THE INVENTION

Other than in the operating examples, or where otherwise indicated, all numbers expressing quantities of ingredients, reaction conditions and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of 1 to 10 is intended to include all sub-ranges between and including the recited minimum value of 1 and the recited maximum value of 10, that is, having a minimum value equal to or greater than 1 and a maximum value of equal to or less than 10.

As used herein, unless otherwise expressly specified, all numbers such as those expressing values, ranges, amounts or percentages may be read as if prefaced by the word "about", even if the term does not expressly appear. Any numerical range recited herein is intended to include all sub-ranges subsumed therein. Plural encompasses singular and vice versa; e.g., the singular forms "a," "an," and the include plural referents unless expressly and unequivocally limited to one referent.

With respect to the present invention, the phrase "chemically stable" as used herein is intended to refer to a dispersion containing one or more active ingredients wherein the active ingredient does not chemically degrade or decompose to an unacceptable degree; i.e., the amount of active ingredient does not decrease by more than 10 percent by weight, preferably 5 percent by weight, compared to its original concentration, after storage of the dispersion at 54° C. for four weeks.

With respect to the present invention, the phrase "physically stable" as used herein is intended to refer to a dispersion containing an active ingredient wherein the disperse phase does not settle, or is easily redispersible if some settling occurs, the two phases are more homogeneous throughout the dispersion, and/or the dispersion demonstrates less syneresis than in an unstable dispersion.

The present invention provides a process for preparing a chemically stable aqueous dispersion of prothioconazole. The process comprises:

(a) introducing prothioconazole to an aqueous medium to yield an aqueous dispersion of prothioconazole; and (b) introducing a sulfur-containing compound to the aqueous dispersion in an amount effective to render the dispersion chemically stable.

The dispersion prepared by the process of the present invention may be provided as an emulsifiable concentrate, suspension concentrate, suspo-emulsion, micro-dispersion, micro-emulsion, directly sprayable or dilutable dispersion, a coatable paste, or dilute emulsion. The continuous phase is aqueous, but other solvents (both polar and non-polar) including alcohols, ketones, petroleum fractions, aromatic or paraffinic hydrocarbons, chlorinated hydrocarbons, liquefied gases, and the like, are suitable for use in combination with the water.

When the dispersion is prepared as a concentrate, the prothioconazole is typically present in the aqueous dispersion in an amount of at least 10 percent by weight, often 25 to 40 percent by weight, based on the total weight of the aqueous dispersion. More often, the dispersion is prepared as a low concentration formulation and the prothioconazole is present in the aqueous dispersion in an amount of 0.05 to 2.0 percent by weight, based on the total weight of the aqueous dispersion. The prothioconazole is usually present in the aqueous dispersion in an amount less than 2.0 percent by weight, such as less than 0.5 percent by weight. It is often present in an amount of 0.1 to 2.0 percent by weight, or 0.1 to 0.5 percent by weight, based on the total weight of the aqueous dispersion.

The sulfur-containing compound is present in the dispersion in an amount effective to render the dispersion chemically stable as defined above. However, such amounts must be within government regulations for additives to agricultural treatment compositions. The compound must therefore be carefully chosen to be effective while maintaining government guidelines for maximum permissible amounts. Antioxidants such as ascorbic acid, tocopherols, and polyphenols were compared to the sulfur-containing compound used in the process of the present invention, and were found to be either ineffective or may require amounts in excess of government mandates when used without the sulfur-containing compound. When the dispersion is prepared as a low concentration formulation, the sulfur-containing compound is typically present in the aqueous dispersion in an amount up to 5 percent by weight, based on the total weight of the aqueous dispersion.

In certain embodiments of the present invention, the sulfur-containing compound comprises a sulfur-containing amino acid or peptide, a sulfur-containing amido acid, a sulfur-containing acid salt, an acid hydrate, a sulfur-containing acid ester such as an alkyl ester, and/or derivatives thereof. Examples of suitable sulfur-containing amino acids include, inter alia, cysteine and homocysteine. Suitable sulfur-containing amido acids include α-mercaptopropionylglycine. Salts of the amino acids may include, for example, hydrochloride salts and sulfuric acid salts. Derivatives of any of the above are also suitable, such as anhydrides and N- and/or S-substituted compounds. Substituents on the nitrogen or sulfur atoms may independently include linear or cyclic alkyl groups such as methyl, ethyl, n-propyl, isopropyl, and the like; aryl groups, aralkyl groups, alkyl carbonyl groups such as acetyl, allyl groups, and similar groups, having from 1 to 20 carbon atoms. Methionine is an example of a suitable S-substituted amino acid. Cysteine is particularly suitable because it also serves as an inert safener.

Sulfur-containing amino acids that contain chiral carbons (e.g., α-amino acids) may be used in the L-form, the D-form, and as racemic mixtures. Such racemic mixtures may contain any ratio of stereoisomers.

In particular embodiments of the present invention, the sulfur-containing compound comprises a mixture of two or more different sulfur-containing compounds having similar chemical structures; for example, the different compounds may have similar functional groups such as a carboxylic acid group, salt group, amino group, or ester group. The different compounds may have homologous alkyl, aryl, aralkyl, or alkyl carbonyl substituents on a carbon, oxygen, nitrogen or sulfur atom in the molecule, and be otherwise similar; for example, an amino acid having N-substituted methyl groups in admixture with the same amino acid having N-substituted ethyl groups. The different compounds may be a mixture of isomers, and in particular instances, may be racemic mixtures of stereoisomers as noted above. The different compounds may be a mixture of a sulfur-containing compound and the disulfide of its close analog, and in particular instances, may be a mixture of L-cysteine with L-cystine dimethyl ester (a mixture of sulfur monomer, RSH, and sulfur dimer, R'S—SR', of similar structure), a mixture of L-cysteine with L-cysteine methyl ester, a mixture of cysteine and D-penicillamine, or a mixture of cysteine and α-mercaptopropionylglycine.

It is believed that the use of a mixture of different sulfur-containing compounds having similar chemical structures may aid in the efficacy of the sulfur-containing compounds by preventing crystallization thereof and possible precipitation from the dispersion of prothioconazole.

The aqueous dispersion may optionally include auxiliary agents commonly used in agricultural treatment formulations and known to those skilled in the art. Examples include antioxidants such as ascorbic acid, penetrants, biocides, preservatives, deodorizers, fragrances, antifreezes and evaporation inhibitors such as glycerol and ethylene or propylene glycol, sorbitol, mineral oil, process oils, sodium lactate, fillers, carriers, colorants including pigments and/or dyes, pH modifiers (buffers, acids, and bases), salts such as calcium, magnesium, ammonium, potassium, sodium, and/or iron chlorides, fertilizers such as ammonium sulfate and ammonium nitrate, urea, and surfactants such as dispersing agents, emulsifiers, wetting agents, defoamers and suspension agents. The aqueous dispersion may also contain other active ingredients such as additional fungicides, insecticides, pesticides, and/or fertilizers known in the art, provided they are compatible with prothioconazole.

Suitable defoamers include all customary defoamers including silicone-based and those based upon perfluoroalkyl phosphinic and phosphonic acids, in particular silicone-based defoamers, such as silicone oils, for example.

Defoamers most commonly used are those from the group of linear polydimethylsiloxanes having an average dynamic viscosity, measured at 25° C., in the range from 1000 to 8000 mPas (mPas=millipascal-second), usually 1200 to 6000 mPas, and containing silica. Silica includes polysilicic acids, meta-silicic acid, ortho-silicic acid, silica gel, silicic acid gels, kieselguhr, precipitated $SiO_2$, and the like.

Defoamers from the group of linear polydimethylsiloxanes contain as their chemical backbone a compound of the formula HO—[Si$(CH_3)_2$—O—]$_n$—H, in which the end groups are modified, by etherification for example, or are attached to the groups —Si$(CH_3)_3$. Non-limiting examples of defoamers of this kind are RHODORSIL® Antifoam 416 (Rhodia) and RHODORSIL® Antifoam 481 (Rhodia). Other suitable defoamers are RHODORSIL® 1824, ANTIMUSSOL 4459-2 (Clariant), Defoamer V 4459 (Clariant), SE Visk and AS EM SE 39 (Wacker). The silicone oils can also be used in the form of emulsions.

The present invention will further be described by reference to the following examples. The examples are merely illustrative of the invention and are not intended to be limiting. Unless otherwise indicated, all parts are by weight.

EXAMPLES

The following examples demonstrate the preparation of chemically stable aqueous dispersions of prothioconazole in accordance with the present invention. Example 1 is a control formulation with no sulfur-containing compound. Examples 2 and 3 demonstrate the addition of cysteine to an aqueous dispersion of prothioconazole at increasing levels. The compositions were placed in an oven at 54° C. for an interval of 1 week, 2 weeks, 3 weeks and 4 weeks. The compositions were then analyzed using HPLC. The results showed significant improvement of chemical stability of prothioconazole in the presence of cysteine.

| Ingredient | Example 1 (Control) | Example 2 | Example 3 |
|---|---|---|---|
| water | 49.55 | 49.55 | 49.55 |
| propylene glycol | 26 | 26 | 26 |
| Atlox4913[1] | 3 | 3 | 3 |
| Toximul TA-15[2] | 4 | 4 | 4 |
| Prothioconazole | 1.54 | 1.52 | 1.51 |
| Tebuconazole[3] | 0.3 | 0.3 | 0.3 |
| Metalaxyl[4] | 0.61 | 0.61 | 0.61 |
| antifoam | 0.02 | 0.02 | 0.02 |
| Butyrolactone Gamma | 2.5 | 2.5 | 2.5 |
| Levanyl Red 2 BX-LF[5] | 12 | 12 | 12 |
| cysteine | 0 | 0.5 | 1.0 |

[1]Surfactant available from Croda
[2]Surfactant available from Stepan Company
[3]Technical Fungicide available from Bayer CropScience
[4]Technical Fungicide available from Nation's Ag LCC
[5]Pigment available from LANXESS Concentration (Percent by Weight) of Prothioconazole by HPLC

|  | 0 time | 1 week | 2 weeks | 3 weeks | 4 weeks |
|---|---|---|---|---|---|
| Example 1 (0% Cysteine) | 1.54% | 1.41% | 1.40% | 1.31% | 1.25% |
| Example 2 (0.5% Cysteine) | 1.52% | 1.54% | 1.54% | 1.49% | 1.45% |
| Example 3 (1.0% Cysteine) | 1.51% | 1.55% | 1.53% | 1.53% | 1.49% |

In comparative Example 4 and 5, the composition of Example 2 was prepared using 0.5 percent by weight sodium ascorbate and ascorbic acid, respectively, both of which are known antioxidants. The compositions were placed in an oven at 54° C. Results are shown below.

Example 4

Sodium Ascorbate

| Time/week | Prothioconazole wt % |
|---|---|
| 0 | 1.44 |
| 1 | 1.30 |
| 2 | 1.34 |
| 4 | 1.20 |

Example 5

Ascorbic Acid

| Time/week | Prothioconazole wt % |
|---|---|
| 0 | 1.43 |
| 1 | 1.30 |
| 2 | 1.28 |
| 4 | 1.12 |

Examples 6 to 10 demonstrate the addition of various compounds to aqueous dispersions of prothioconazole in a medium of 43% acetonitrile and 57% water. Example 6 is a control with no additional compounds. Example 7 is a comparative example using 0.116 percent by weight (106.54 mg) ascorbic acid. Examples 8 and 9 are illustrative of the present invention using 105.32 mg cysteine ester and 103.82 mg cysteine hydrate, respectively (0.116 percent by weight).

Zero time data was generated for all of these compositions, and they were placed in a 54° C. oven and a refrigerator. Results are posted below. The % is the weight % the of initial amount of prothioconazole.

| 54° C. | 6 | 7 | 8 | 9 |
|---|---|---|---|---|
| Zero Time | 99.54% | 98.87% | 99.51% | 98.58% |
| 1 Week | 99.34% | 83.97% | 98.67% | 98.44% |
| 2 Weeks | 98.81% | 79.61% | 100.22% | 100.65% |

| 5° C. | 6 | 7 | 8 | 9 |
|---|---|---|---|---|
| Zero Time | 99.54% | 98.87% | 99.51% | 98.58% |
| 1 Week | 100.34% | 96.89% | 99.71% | 100.84% |
| 2 Weeks | 99.57% | 83.45% | 100.50% | 101.01% |

Whereas particular embodiments of this invention have been described above for purposes of illustration, it will be evident to those skilled in the art that numerous variations of the details of the present invention may be made without departing from the invention as defined in the appended claims.

What is claimed is:

1. A process for preparing a chemically stable aqueous dispersion of prothioconazole, the process comprising:
   (a) introducing prothioconazole to an aqueous medium to yield an aqueous dispersion of prothioconazole; and
   (b) introducing a sulfur-containing compound to the aqueous dispersion in an amount effective to render the dispersion chemically stable,
   wherein the sulfur-containing compound comprises cysteine or homocysteine, a salt thereof, a hydrate thereof, or an ester thereof,
   wherein the sulfur-containing compound is present in the aqueous dispersion in an amount up to 5 percent by weight, based on the total weight of the aqueous dispersion.

2. The process of claim 1, wherein the prothioconazole is present in the aqueous dispersion in an amount of 0.05 to 2.0 percent by weight, based on the total weight of the aqueous dispersion.

3. The process of claim 1, wherein the sulfur-containing compound comprises a mixture of two or more different sulfur-containing compounds.

4. The process of claim 3, wherein the different sulfur-containing compounds have the same or different functional groups selected from carboxylic acid groups, salt groups, amino groups, or ester groups.

5. The process of claim 3, wherein the sulfur-containing compound comprises a mixture of isomers.

6. A chemically stable aqueous dispersion of prothioconazole, comprising:
(a) prothioconazole present in an aqueous medium; and
(b) a sulfur-containing compound present in an amount effective to render the dispersion chemically stable,
wherein the sulfur-containing compound comprises cysteine or homocysteine, a salt thereof, a hydrate thereof, or an ester thereof,
wherein the sulfur-containing compound is present in the aqueous dispersion in an amount up to 5 percent by weight, based on the total weight of the aqueous dispersion.

7. The dispersion of claim 6, wherein the prothioconazole is present in the aqueous dispersion in an amount of 0.05 to 2.0 percent by weight, based on the total weight of the aqueous dispersion.

8. The dispersion of claim 6, wherein the sulfur-containing compound comprises cysteine methyl ester.

9. The dispersion of claim 6, wherein the sulfur-containing compound comprises a mixture of two or more different sulfur-containing compounds.

10. The dispersion of claim 9, wherein the sulfur-containing compound comprises a mixture of cysteine and cysteine methyl ester, a mixture of cysteine and D-penicillamine, or a mixture of cysteine and a-mercaptopropionylglycine.

11. The dispersion of claim 9, wherein the different sulfur-containing compounds have the same or different functional groups selected from carboxylic acid groups, salt groups, amino groups, or ester groups.

12. The dispersion of claim 9, wherein the sulfur-containing compound comprises a mixture of isomers.

13. The dispersion of claim 9, wherein the sulfur-containing compound comprises a mixture of sulfur monomer and sulfur dimer.

14. The dispersion of claim 13, wherein the sulfur-containing compound comprises a mixture of L-cysteine and L-cystine dimethyl ester.

* * * * *